United States Patent [19]

Pompei et al.

[11] 4,100,048

[45] Jul. 11, 1978

[54] POLAROGRAPHIC CELL

[75] Inventors: Jean Pompei, Noisy-le-Roi; Francis Pierrot, Rueil, both of France

[73] Assignee: U.S. Philips Corporation, New York, N.Y.

[21] Appl. No.: 693,490

[22] Filed: Jun. 7, 1976

Related U.S. Application Data

[63] Continuation of Ser. No. 506,249, Sep. 16, 1974, abandoned.

[30] Foreign Application Priority Data

Sep. 20, 1973 [FR] France .................. 73 33743

[51] Int. Cl.² ................................ G01N 27/46
[52] U.S. Cl. ............................... 204/195 P
[58] Field of Search .............. 204/195 P, 1 P; 324/29; 128/2 E

[56]  References Cited

U.S. PATENT DOCUMENTS

| 3,227,643 | 1/1966 | Okun et al. | 204/195 P |
| 3,711,395 | 1/1973 | Plank et al. | 204/195 P |
| 3,714,015 | 1/1973 | Niedrach | 204/195 P |
| 3,763,850 | 10/1973 | Gaudebout et al. | 128/2 E |

Primary Examiner—G. L. Kaplan
Attorney, Agent, or Firm—Frank R. Trifari; Norman N. Spain

[57] ABSTRACT

A polarographic cell for measuring partial pressure of oxygen in a fluid in which the detector electrode and the reference electrode are immersed in an electrolyte at least partially absorbed in a rigid insulating material.

5 Claims, 3 Drawing Figures

POLAROGRAPHIC CELL

This is a continuation of application Ser. No. 506,244, filed Sep. 16, 1974 and now abandoned.

The present invention relates to a polarographic cell intended for measuring the partial pressure of a gas, particularly oxygen in a fluid, which cell has two electrodes, namely a detection electrode and a reference electrode immersed in an electrolyte, both electrodes and the electrolyte being separated from the said fluid by an insulating membrane permeable to the gas to be measured.

it is known that in a polarographic cell the current intensity (polarographic current) upon connection to a voltage source is a function of the pressure of the fluid present outside the membrane.

In the absence of the said reactive gas the electric current adjusted at the instant of closure of the said circuit decreases quickly to substantially zero: the cell is then polarized. The elements of the cell, electrodes and electroylte are chosen to be such that the reactive gas at the detection electrode acts as a depolarizer. The value of the polarographic current indicates the partial pressure of the reactive gas in the fluid after calibration of the cell.

Three important parameters characterize the quality level of a polarographic cell: adjusting time, sensitivity and what is known in the art as "flow sensitivity".

The adjusting time or response time is the time necessary for the cell to adjust after a modification of the partial pressure of the gas to be analyzed.

The electrical sensitivity is the value of the variation in the polarographic current intensity through the cell at a given variation of the partial pressure of the gas.

The flow sensitivity indicates the dependence of the polarographic current on the diffusion which occurs when the gas flows the membrane in the absence of a relative movement of the cell relative to the surrounding gas mixture. In the relevant case the polarographic current may be influenced by sudden changes which have an adverse effect on the measurement. In order to reduce the time constant of a polarographic cell and to increase its electrical sensitivity it may be expected that it is advantageous to limit the thickness of the membrane as much as possible.

On the other hand it has been found that as the membrane is located closer to the direction electrode, hence the film of electrolyte is less thick, the response time is shorter and the electrical sensitivity is greater.

Finally the polarographic current is less sensitive to flow as the membrane adheres better to the detection electrode and the detection electrode has a larger surface.

Considerations of a mechanical and physical nature oppose the choice of a very thin membrane.

In the polarographic cells of known structure the membrane is a foil of polyethylene, polypropylene or polytetrafluoroethylene and is at least partly subjected to the mechanical pressure due to the column of electrolyte even when it is present in a gel form. Consequently the membrane must have a thickness of at least several microns, preferably even several dozen microns.

Such a thickness is also necessary because the membrane must adhere satisfactorily to the detection electrode because otherwise gas bubbles might be formed between the two elements so that the polarographic current might be interrupted. Due to ageing of the membrane or by temperature fluctuation of the cell the membrane is often weakened so that gas bubbles may be formed between the membrane and the electrode.

U.S. Patent Specifications No. 3,278,408 proposes a bipartite membrane which is an active membrane of polytetrafluoroethylene having a thickness of approximately 25 $\mu$m and a supporting membrane of a silicon elastomer having a thickness of approximately 125 $\mu$m. The active membrane is present between the detection electrode and the supporting membrane. It is floating, i.e. it is not fixed to any other part of the construction. The active membrane is pressed against the detection electrode by the elastic pressure exerted on the supporting membrane while the supporting membrane is retained by two securing rings simultaneously preventing leakage of the electrolyte. Although the stability of this cell and the reproducibility of the measurements performed with this cell are considerably improved, the cell has the drawback of a long adjusting time and a rather low sensitivity.

According to French Patent Specification No. 2,147,344 electrodes in the form of thin coatings on a silicon substrate are used. This substrate is present in an envelope whose side facing the electrodes consists of a membrane of polytetrafluoroethylene having a thickness of several microns. The electrolyte is present between the membrane and electrodes.

This cell gives stable and reproducible results due to the large contact surface of the detection electrode and the large distance between the membrane and the detection electrode. Variations in the distance due to deformation of the membrane are thus negligible. However, the distance between membrane and electrode and the thickness of the membrane are unfavourable with respect to the adjusting time and the electrical sensitivity of the cell.

The present invention has for its object to provide a polarographic cell in which all properties referred to are favourable, i.e. a short adjusting time, a great sensitivity, stability and reproducibility of the measurements to be performed.

According to the invention a polarographic cell for measuring the partial pressure of a gas particularly oxygen in a fluid, which cell has two electrodes, a detection electrode and a reference electrode immersed in an electrolyte and in which bith electrodes and the electrolyte are separated from the said fluid by an insulating membrane permeable to the gas to be measured is characterized in that the electrolyte is at least partly immobilized by absorption thereof in a rigid insulating porous material.

According to a further elaboration of the invention the said rigid material may be used as a substrate and at least the detection electrode consists of a thin coating on the surface of this element.

On the other hand the rigid material may alternatively be used as a support for the membrane. According to a further elaboration of the invention the membrane, likewise in the shape of a thin coating is partly supported directly by the rigid material itself and partly by the detection electrode and optionally the reference electrode.

All these steps contribute to a satisfactory solution of the construction problems of a polarographic cell.

The mechanical force necessary to retain the electrolyte taken up in the pores of the rigid material, which electrolyte can, however, alternatively be stored in a reserve outside the said material is completely provided by this rigid material. As a result the membrane which is not subject to any mechanical tension may be made considerably thinner, On the other hand the membrane forms an integral part with the support and is not deformed. The distance between membrane and detection electrode remains constant while the two members of the cell are in contact with each other.

It is remarkable that the absence of an electrolyte film between the said membrane and the said detection electrode does not hamper the operation of the cell in any way. The exchange between the gas molecules from the fluid outside the cell and the detection electrode takes place in a plane on the edge of the said electrode; in the presence of electrolyte on this edge this exchange takes place to an amply sufficient extent.

Preferably and in order to simplify this exchange the detection electrode is formed in such a manner that its circumference is enlarged. There is a large contact line between the gas molecules and the detection electrode. As compared with the known cells all the improvements in the polarographic cell according to the invention make this cell very attractive.

As the membrane has a slight thickness, the diffusion time of the gas is reduced. Since the detection electrode is placed immediately behind the membrane, the flow time of the gas between membrane and electrode is negligible. The adjusting time of the cell is therefore short, in the order of 5 to 10 times shorter than that of a cell of the conventional construction. The electrical sensitivity is approximately a factor of 10 larger.

As regards the construction it is advantageous that there are no fixation elements and stress on the membrane. As this membrane has the form of a thin coating it adheres to the support without fixation elements being necessary. The construction of the cell is therefore much simpler.

Since the tension of the membrane remains constant and exchange is regularly effected at the edge of the detection electrode, the measurements with the cell according to the invention are very stable and reproducible under the same circumstances.

According to a very favourable embodiment of a polarographic cell according to the invention the rigid insulating porous material which is the support for the electrodes and the membrane consists of a disc of sintered glass or ceramic material, for example, sintered aluminum oxide.

The disc of sintered glass is concentrically surrounded by a ring of normal glass to which it is fused and in which two electrical conductors are sealed, one for each electrode of the cell.

The disc of sintered glass has a smaller thickness than the concentrical ring in the sence that the assembly has the shape of a tray.

The two electrodes of the cell are deposited on the front face of the device which is polished in advance and at the height of which the said electrical conductors are located. The detection electrode is deposited in the form of a thin coating of, for example, gold and the reference electrode is likewise deposited in the form of a thin coating, for example, silver. The shape of these electrodes is not important, but the detection electrode is to have a fairly large surface. It should preferably formed as a double comb. Each of the electrodes is connected to an electrical conductor.

The entire front face of the device (electrodes, disc and concentrical ring) is coated with a thin coating of polytetrafluoroethylene of not more than 0.5 $\mu$m which constitutes the membrane and is permeable to the gas whose partial pressure is to be measured.

The membrane is provided, for example, by high frequency sputtering of a disc of polytetrafluoroethylene.

The tray present on the other side of the cell is filled with a suitable electrolyte such as a saturated solution of potassium chloride in water and sealed with a cover, for example, a glass plate which is stuck to the edge of the concentrical glass ring.

The electrolyte is subsequently allowed to flow into the pores of the disc of sintered flass until the front face of this disc is reached. The rest of electrolyte in the tray forms a reserve which maintains the disc impregnated.

It is to be noted that in spite of the small thickness of the membrane, this membrane is not permeable to vapour of the electrolyte which is especially a property of polytetrafluoroethylene deposited by means of the above-mentioned cathode sputtering method.

It is to be noted that United Kingdom Patent Specification No. 1,074,005 described a cell having a part of porous material, notably sintered glass, but this part is used in this cell to retain the electrodes or for dividing the said cell in compartments. It does not play any role in retaining electrolyte as in the case of the present application; the cell according to this United Kingdon Patent Specification is used without an electrolyte. The component of porous material without a membrane — is in direct contact with a gas atmosphere.

According to a further embodiment of a cell according to the invention the rigid insulating porous material has the shape of a cylinder or of a prism having a polygonal base and consists of, for example, sintered aluminum oxide. The detection electrode is deposited on the side face of this cylinder and a silver wire is connected into a narrow axial cavity of the said cylinder, which silver wire constitutes the reference electrode.

The detection electrode as well as the uncoated parts of the side surface of the cylinder of aluminum oxice are coated with a thin coating of polytetrafluoroethylene.

The cylinder is impregnated through its base and its top with electrolyte. The base and the top are closed with caps of wax and the conductors connected to the electrodes are passed through one of them.

A polarographic cell according to this embodiment has a very broad diffusion front for gas passing through the membrance and a very large exchange surface at the level of the detection electrode. Its drawback is that it does not have any reserve electrolyte, but the advantage of a great simplicity of construction.

The invention will be described in greater detail with reference to the accompanying drawings.

Figure 1:
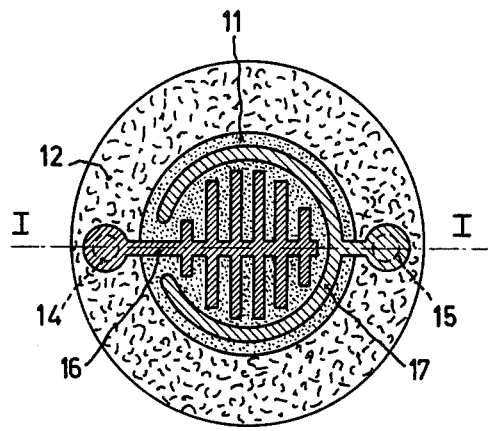
FIG. 1 is a plan view of a polarographic cell according to a first embodiment.
Figure 2:
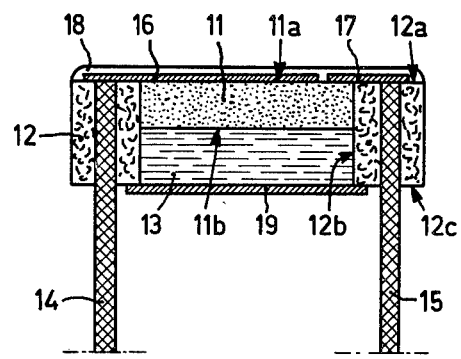
FIG. 2 is the same polarographic cell in a cross-section taken on the line II of FIG. 1.

The polarographic cell according to FIGS. 1 and 2 is built on a disc of sintered glass 11 whose side edge is fused to a flat ring 12 of insulating, nonporous material such as glass. Preferably lead glass of the kind used for moulding the base plate of electron valves is used for this purpose.

The disc 11 has a smaller thickness than that of the ring 12 so that as a result of the front faces 11a of the said disc and 12a of the said ring being coplanar a tray 13 is formed on the rear side of the assembly, which tray is bounded on its lower side by the rear face 11b of the disc 11 and on its sides by the inner edge 12b of the ring 12.

According to a preferred direction in the ring 12, which direction is at right angles thereto, two metal connection conductors 14 and 15 are sealed one end of each of which is at the same level as the face 12a of the said ring. The face 11a of the disc 11 suports the two electrodes of the cell in the form of thin metal deposits: the detection electrode 16 having a large surface is formed as a double comb having unequal teeth and the reference electrode 17 constitutes a half moon surrounding the said detection electrode.

The detection electrode 16 is connected to the corresponding end of the conductor 14 and the reference electrode 17 is connected to the end of the conductor 15.

The electrode 16 and 17 and the bare parts of the faces 11a of the disc 11 and 12a of the ring (for the ring at least on the edge of this ring surrounding the seal) support a membrane 18 in the form of a thin coating of synthetic resin material, for example, polyethylene or polypropylene, preferably polytetrafluoroethylene.

The tray 13 contains a suitable electrolyte impregnating the porous disc 11. The electrodes 16 and 17 are thus immersed in this electrolyte whose level is below the membrane 18.

The tray 13 is closed by a cover 19, for example, a glass plate whose edges are sealed to the rear face 12c of the ring 12.

The conductors are preferably protected by an insulating coating of, for example, enamel. Thus the cell as such can be placed in the fluid to be analysed.

For the purpose of illustration the most important details of a polarographic cell of the said construction will be described hereinafter.

The disc of sintered glass 11 has a diameter of 10 mm and a thickness of 2 mm. The ring 12 has a diameter of approximately 18 mm and a thickness of 5 mm. The tray 13 thus has depth in the order of 3 mm.

Disc 11 is cemented to ring 12 by means of, for example, the cement known by the trade name "TORR-SEAL" manufactured by the firm of "VARIAN ASSOCIATES".

The detection electrode 16 consists of a thin film of gold having a thickness of 0.8 $\mu$m (0.7 to 0.9 $\mu$m). It comprises two symmetrical faces having 15 teeth with a width of 0.2 mm each and arranged with a pitch of 0.4 mm.

The reference electrode 17 consisting of silver having a thickness of 0.8 $\mu$m (0.7 to 0.9 $\mu$m) is arranged on a circumference whose average diameter is 9.5 mm and has a width of 0.2 mm.

The ends of each of the teeth of the electrode 16 are remote over a distance of 0.2 mm (0.15 to 0.25 mm) from the edge facing the electrode 17. The short distance between these two electrodes 16 and 17 makes it possible for the internal resistance of the cell to be low.

The polytetrafluoroethylene membrane 18 has a thickness of 0.4 $\mu$m (0.3 to 0.5 $\mu$m).

The electrolyte is, for example, a saturated solution of potassium chloride in deionized water.

The cover 19 closing the tray 13 is a glass plate having a thickness of 0.3 mm. This plate is secured to the ring 12 by means of an adhesive known under the trade name of "CYANOLIT".

Such a polarographic cell is absolutely liquid-tight and may be used for measuring the partial pressure of oxygen in water.

This use is of course not limited and may be extended to investigations of liquids other than water and gases other than oxygen. The cell according to the invention may especially be used in gaseous media. In each case it is sufficient to adapt the nature of the metal deposits of the electrodes and that of the electrolytic material accordingly.

For manufacturing the cell shown in FIGS. 1 and 2 the electrodes 16 and 17 of gold and silver are provided by means of thermal evaporation with the aid of a nickel mask on the flat polished sides 11a and 12a.

The thin coating 18 of a polytetrafluoroethylene is provided by means of high frequency cathode sputtering in an argon atmosphere of $5.10^{-3}$ Torr (13 MHz) with a power of 350 Watts.

The cell is filled with potassium chloride under a nitrogen atmosphere in a space protected from dust. The same precautions are taken when sealing the cover 19.

Figure 3:
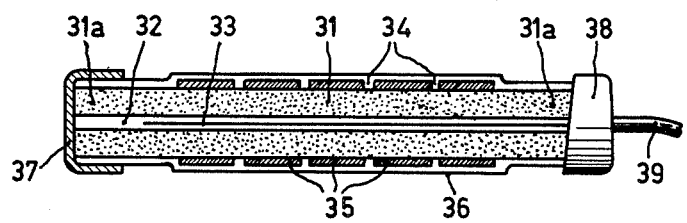
FIG. 3 is a partial cross-section of a polarographic cell according to the invention in a second embodiment.

The polarographic cell according to a second embodiment shown in FIG. 3 is formed on a rod of porous ceramic material, for example, aluminium oxide.

The aluminum oxide rod 31 has the shape of a cylinder of small diameter. In this cylinder a narrow axial cavity 32 is provided in the longitudinal direction in which the reference electrode 33 consisting of silver wire accommodated.

A film of gold having a thickness of 0.8 $\mu$m is deposited on part of the side surface of the rod 31 which is longitudinally, transversely or helically provided with grooves 34 and the assembly of which constitutes the detection electrode 35.

The assembly of side surface of the rod 31, electrode 35, grooves 34 and ends 31a of the said rod is coated with a deposit having a thickness of 0.5 $\mu$m of polytetrafluoroethylene constituting the membrane 36.

The rod 31 is impregnated with an electrolyte. The ends are sealed by means of two plugs 37 and 38 of, for example, a wax or of a thermosetting material. The connection conductors are passed to the electrodes 33 and 35 through the material 38 and in the cable 39.

a polarographic cell of FIG. 3 may be preferably be manufactured in very small dimensions, which makes it suitable for medicine especially for measuring the partial pressure of oxygen in blood.

The large accessible surface of the detection electrode 35 gives the cell a great electrical sensitivity. It is of course important to use a rod 31 whose length is large relative to the diameter in order to reduce the internal resistance of the cell.

What is claimed is:

1. In a polarographic cell particularly adapted for the measurement of the partial pressure of a gas in a fluid comprising a detection electrode and a reference electrode immersed in an electrolyte and an insulating membrane, permeable to the gas being measured, separating the electrodes and the electrolyte from said fluid, the improvement wherein the electrolyte is at least partly immobililized by absorption in a rigid, insulating, porous material selected from the group consisting of sintered glass and sintered ceramic material and at least the detection electrode is in the form of a coating on the surface of said rigid material, said coating being thinner than said rigid material.

2. The polarographic cell of claim 1 wherein the insulating membrane is partially provided on the rigid material and at least partially on the detection electrode.

3. The polarographic cell of claim 1 wherein the rigid insulating material is a cylindrical rod the side face of which supports the detection electrode and the reference electrode is in the form of a wire positioned along the longitudinal axis of said rod shaped rigid insulating material.

4. A polarographic cell as claimed in claim 1, characterized in that the rigid, insulating, porous material consists of sintered glass.

5. A polarographic cell as claimed in claim 1, characterized in that the rigid, insulating, porous material consists of sintered aluminum oxide.

* * * * *